United States Patent [19]
Kondo et al.

[11] Patent Number: 5,002,768
[45] Date of Patent: Mar. 26, 1991

[54] RODENT-REPELLENT MICROCAPSULES AND PREPARATIONS THEREOF

[75] Inventors: Takeshi Kondo, Takarazuka; Osamu Ueda, Nara; Yoshiya Fukakusa, Asaka; Masafumi Moriwaki, Hachioji; Hideki Fuziwara, Musashino, all of Japan

[73] Assignees: Tanabe Seiyaku Co., Ltd., Osaka; Toppan Moore Co., Ltd., Tokyo, both of Japan

[21] Appl. No.: 279,295

[22] Filed: Nov. 30, 1988

Related U.S. Application Data

[63] Continuation of Ser. No. 813,673, Dec. 26, 1985, abandoned.

[30] Foreign Application Priority Data

Dec. 28, 1984 [JP] Japan ............................. 59-59275278
Dec. 9, 1985 [JP] Japan ............................. 60-60276276
Dec. 9, 1985 [JP] Japan ............................. 60-60276277
Dec. 9, 1985 [JP] Japan ............................. 60-60277622

[51] Int. Cl.$^5$ ....................... A01N 25/28; B01J 13/14
[52] U.S. Cl. .................................. 424/408; 174/120 C; 264/4.7; 424/405; 424/406; 424/438; 424/455; 424/462; 514/963; 524/98
[58] Field of Search ................... 264/4.7; 428/402.21; 424/405, 406, 438, 455, 462, 408

[56] References Cited

U.S. PATENT DOCUMENTS 3,218,231 11/1965 Harkin et al. .................. 514/328 X
3,303,046 2/1967 Chebiniak et al. ............. 503/226 X
3,516,941 6/1970 Matson ............................ 264/4.7 X
4,557,755 12/1985 Takahashi et al. .............. 264/4.7 X

FOREIGN PATENT DOCUMENTS 0110233 8/1979 Japan ................................. 514/328

OTHER PUBLICATIONS

*The Condensed Chemical Dictionary*, Tenth Edition, revised by G. G. Hawley, Van Nostrand Reinhold Co., New York (1981), pp. 162, 330, 348–350, 358, 359, 372, 388, 1044, 1056 and 1057.

Primary Examiner—Richard D. Lovering
Attorney, Agent, or Firm—Weingarten, Schurgin, Gagnebin & Hayes

[57] ABSTRACT

There are herein disclosed rodent-repellent microcapsules in which a core material is coated with a wall material of the microcapsules, the core material being a solution containing cycloheximide; a rodent-repellent resin composition comprising said microcapsules; a rodent-repellent coating material comprising said microcapsules; and a rodent-repellent adhesive comprising said microcapsules.

19 Claims, No Drawings

RODENT-REPELLENT MICROCAPSULES AND PREPARATIONS THEREOF

This application is a continuation of application Ser. No. 06/813,673, filed Dec. 26, 1985, now abandoned.

BACKGROUND OF THE INVENTION

(1) FIELD OF THE INVENTION

The present invention relates to microcapsules filled with a solution containing cycloheximide (hereinafter referred to simply as CHI) and preparations thereof, and more specifically it relates to microcapsules filled with CHI and their preparations in which drawbacks of a conventional CHI crystal practically employed as rodent repellents and antimicrobials for plants are overcome.

(2) DESCRIPTION OF THE PRIOR ART

As conventional products to which the technique of microcapsules is applied, there are many examples such as pressure-sensitive copying papers, heat-sensitive recording papers, medicines, animal medicines, argicultural chemicals, preventive medicines against epidemics, fertilizers, cosmetics and adhesives Further, examples in which the microcapsule technique is applied to insecticides are also present in various forms, and for example, the following preparations are known:

(a) a warfarin raticide (trade name Raze)
(b) an ant repellent (trade name Merexbait)
(c) cockroach insecticide (trade name Diazinon MC; suspension) and
(d) a white ant repellent.

Of these preparations, the raticide in the preceding paragraph (a) is encapsulated for the purpose of causing rats to easily eat the warfarin raticide, and the ant repellent in the preceding paragraph (b) is also encapsulated for the improvement in a residual effect of the toxic food agent for ants.

In addition thereto, there is also known the encapsulation of microbiological agricultural chemicals and virus agricultural chemicals which have the residual effect and which can adjust the release of a component, but the technique of encapsulating CHI has been found nowhere.

The mechanism of the rodent-repellent effect of CHI can be presumed as follows: Rats dislike the taste of CHI and are extremely repelled by it. Once the rats have experienced this taste, they will have, in memory, a peculiar odor of CHI which human beings do not feel, and will afterward keep away from CHI by the odor alone.

Next, reference will be made to use examples of a conventional CHI crystal in which the above-mentioned rodent-repellent effect of CHI is utilized.

One example in which the CHI crystal is used is a rodent-repellent cable cover. Such cable covers can be made by kneading the CHI crystal into polyvinyl chloride (PVC) in order to give a rodent-repllent treatment to PVC, and by molding and processing it. A temperature and a time necessary for the molding is 150 to 200° C. and 10 to 30 minutes, respectively, and it has been confirmed that a repellent effect, i.e., an activity (hereinafter referred to as potency) of CHI is deteriorated owing to the heat treatment and/or is lost because of a presence of hydrogen chloride generated in the PVC manufacturing process and a remaining free hydrochloric acid. For this reason, if the rodent-repellent cables having the sufficient potency are contemplated, the CHI crystal must be used in a previously increased amount However, this strategy is not economical from the fact that the CHI crystal is a very expensive reagent. That is the reason why providing CHI with heat resistance and chemical resistance is required The same may be said of rodent-repellent coating compositions which are materials for the rodent-repellent cable covers.

Additionally, even after the manufacture of the rodent-repellent cables, there are problems such as a transfer (bleeding phenomenon) of the CHI crystal present in the PVC toward the surfaces of the cable covers along with the lapse of time, a deterioration in the rodent-repellent effect due to the outflow of the dissolved CHI crystal from the cable covers, and inconveniences from the viewpoints of safety and sanitation for men who handle the cables In consequence, the CHI preparations in which no bleeding phenomenon occurs in PVC are now desired.

Another example in which the CHI crystal is employed is a CHI coating composition. In general, such CHI coating compositions are directly applied on objects for which the rodent-repellent treatment is necessary. In this case, the CHI potency would decline owing to chemical properties of the objects to be applied thereon, and if the objects are articles which are used outdoors, the CHI crystal will be dissolved out with rainwater because of being water-soluble, with the result that the rodent-repellent effect will be lost. That is the reason why supplying CHI with water resistance is required.

It has also been confirmed that CHI will lose its potency in an aqueous solution with time (in the case of the aqueous CHI solution having a pH of 7, 100% of the potency was lost at 37° C. in 3.5 months). Accordingly, CHI must be provided with water resistance and alkali resistance, when desired. Furthermore, since CHI is decomposed with soil-borne bacteria, the property of being resistant to the soil bacteria is also to be given thereto, if utilized as agricultural chemicals.

As be definite from the foregoing, when used in the form of crystal, CHI is very unstable and will lose the potency by its properties themselves, depending upon its usage. The employment of a large amount of CHI which is expensive is not economical, and thus it is fair to say that CHI is very inconvenient to deal with.

SUMMARY OF THE INVENTION

An object of the present invention is to provide microcapsules filled with CHI which are capable of removing a variety of drawbacks such as the deterioration in the potency of crystalline CHI under various circumstances, the decline in a rodent-repellent effect due to a CHI bleeding phenomenon, the loss of the CHI crystal owing to its dissolution in water and the decompositon of CHI with soil-borne bacteria in the case that CHI is used in the form of crystal, and is to provide preparations of the above-mentioned microcapsules.

Another object of the present invention is to provide microcapsules having several times as much an efficacy as that of the case where the conventional CHI crystal is used directly and intactly, and is to provide preparations thereof.

Still another object of the present invention is to provide CHI preparations excellent in heat resistance and chemical resistance.

The inventors of the present application have paid much attention to the fact that CHI has heretofore been only considered to be crystalline and has also been only used in the form of crystal, and have researched in many ways. As a result, the present invention of microcapsules, which can be effectively and economically used as rodent-repellents and as their preparations, have been achieved by dissolving CHI in a solvent scarcely deteriorating the potency of CHI and by filling, with a CHI solution, microcapsules the walls of which are made from a material scarcely declining the potency of CHI.

The microcapsules filled with CHI of the present invention contain about 0.25 to 50 w/w%, preferably about 0.5 to 30 w/w%, more preferably about 2 to 20 w/w% of CHI based on the microcapsules.

It has further been found that when CHI is encapsulated and is added to a resin, a coating composition, an adhesive and the like, the resultant preparations can retain a strong rodent-repellent effect for a long period of time, and when processed for various uses, CHI will be also kept stable.

Accordingly, the present invention is concerned with a rodent-repellent resin composition containing about 0.1 to 25 w/w%, preferably about 0.17 to 20 w/w%, more preferably about 0.5 to 6.0 w/w% of the microcapsules filled with CHI based on the resin component Further, the present invention is concerned with a rodent-repellent coating composition containing microcapsules filled with CHI so that an application amount of CHI may be within the range of about 0.05 to 2.0 g/m$^2$, preferably about 0.1 to 0.7 g/m$^2$, more preferably about 0.2 to 0.5 g/m$^2$.

Furthermore, the present invention is concerned with a rodent-repellent adhesive containing microcapsules filled with CHI so that an application amount of CHI may be within the range of about 0.05 to 3.0 g/m$^2$, preferably about 0.1 to 1.0 g/m$^2$, more preferably about 0.3 to 0.7 g/m$^2$.

DESCRIPTION OF THE PREFERRED EMBODIMENT

(Microcapsules Filled with CHI)

Microcapsules, in which a core material of a CHI-containing solution and a wall material for coating the core material therewith are employed, can be prepared by any known production technique Examples of methods for preparing such microcapsules include an interfacial polymerization method, an in situ method, a coacervation method, a liquid-in-curing-/coating method (an orifice method), a liquid-in-drying method and a spray/graining method. The above-mentioned interfacial polymerization method comprises causing a polymerization reaction of a monomer soluble in a solvent in which CHI is dissolved or dispersed and another monomer soluble in a dispersing medium for forming a continuous phase at interfaces between two phases of these monomers in order to form microcapsules in which each part of the solution containing CHI is confined by a wall of the resultant polymer. Further, the above-mentioned in situ method comprises first feeding a monomer from either a continuous phase or a discontinuous phase and then carrying out a polymerization reaction at an interface.

The CHI solvent used in the present invention has to satisfy the requirement that CHI is chemically stable in the solvent, i.e., that the solvent does not impair the stability of the CHI Potency. In consequence, the solvents satisfying this requirement and having a suitable dissolving power to CHI are usable in the present invention. Examples of such usable solvents include alcohols such as methyl alcohol, ethyl alcohol, propyl alcohol and butyl alcohol; ketones such as acetone, methyl ethyl ketone (MEK), methyl isobutyl ketone (MIBK), ethyl butyl ketone and cyclohexanone; ethers such as ethyl ether, butyl ether, amyl ether, hexyl ether, ethyl vinyl ether, cellosolve and carbitol; aliphatic and aromatic hydrocarbons such as hexane, heptane, octane, benzene, toluene, xylene and cyclohexane; mineral oils such as kerosene, light and paraffin oil; esters such as acetate, propionate, butyrate, lactate, oxalate, crotonate, salicylate, benzoate, phthalate, adipate, sebacate and phosphate; and In the case that a high boiling point, non-volatility and hydrophobicity are necessary as the requirements of the solvent in view of the potency stability of CHI, a method of the capsule production and/or a use morphology of the capsules filled with CHI, the above-mentioned ester resin or low-molecular epoxy resin should be employed as the solvent.

The esters are preferably selected from the group consisting of phthalates such as dimethyl phthalate, diethyl phthalate, dibutyl phthalate, diheptyl phthalate, dioctyl phthalate, diisodecyl phthalate, butyl benzyl phthalate, dimethyl isophthalate, di-2-ethylhexyl phthalate, ditridecyl phthalate and dinormal alkyl phthalate; adipates such as diisobutyl adipate and dioctyl adipate; sebacates such as dibenzyl sebacate and dioctyl sebacate; and phosphates such as triphenyl phosphate, tricresyl phosphate, trioctyl phosphate and octyldiphenyl phosphate.

Further, as the low-molecular epoxy resins, epoxy resins having molecular weights of 400 or less are preferable. Examples of such preferable epoxy resins include Epicoat 815, 816 and 818 (trade names; Shell Petrochemical Co., Ltd.). The usable solvents are not limited to the compounds just mentioned.

An amount of CHI in the solvent is suitably within the range of about 0.25 to 50 w/w%, preferably 0.5 to 30 w/w%, more preferably about 2 to 20 w/w%, from economical and effective viewpoints, based on the microcapsules.

The capsule wall materials for encapsulating the above-mentioned CHI solution are polymers produced from reactive materials of monomers and low-molecular prepolymers, and suitable examples of such wall materials include aminoplasts such as urea resins, melamine resins, mixed urea and melamine resins, phenolic resins, polyamides, polyesters, polyureas and polyurethanes, and phenolic resins, polyesters. Such capsule wall materials may be suitably selected in view of various conditions at the use of the capsule preparations, and from economical and other viewpoints.

(Rodent-Repellent Resin Composition)

In a rodent-repellent resin composition of the present invention, usable resins containing CHI microcapsules are not particularly limited Examples of the usable resins include thermoplastic resins, thermosetting resins, synthetic rubbers and natural resins.

Concretely speaking, examples of the thermoplastic resins include vinyl resins such as polyvinyl chloride, polyvinyl acetate, polyvinylidene chloride and polyvinyl alcohol; petroleum resins such as polyethylene, polypropylene and polybutene; acrylic resins such as methacrylic resin and polyacrylonitrile; styrol resins such as polystyrol; ABS resins; and polyamide resins.

In view of application fields of the rodent-repellent resin compositions, particularly useful thermoplastic resins include polymers and copolymers formed from monomers having vinyl groups, i.e., polyvinyl chloride, polyvinyl acetate, polyvinylidene chloride, polyvinyl alcohol, ethylene-vinyl acetate copolymer, crosslinked polyethylene, polystyrene, polyethylene and ethylene-acrylic acid copolymer.

Examples of the thermosetting resins include phenolic resins, urea resins, melamine resins, polyesters, polyurethanes and epoxy resins. Further, examples of the synthetic rubbers include diene, olefin, acrylic, urethane, silicon, fluorine series rubbers, and their concrete examples include polybutadiene, SBR, NBR, butyl rubbers, chloroprene rubbers, polyisobutylene rubbers, methylene rubbers, propylene rubbers and silicon rubbers Moreover, examples of the natural resins include copal and rosin.

Among these resins, particularly preferable examples include polyvinyl chloride series, polyethylene, polystyrene, phenolic resins, epoxy resins and aminoplast For the purpose of securing processing characteristics and stability, a plasticizer, a stabilizer, a lubricant, a colorant, a flame retardant, a filler, an antioxidant and other suitable additives may be added to the resin The CHI microcapsules used in the present invention may be prepared by the undermentioned process, and a content of the microcapsules in the resin is generally within the range of about 0.1 to 25 w/w%, preferably about 0.17 to 20 w/w%, more preferably about 0.5 to 6.0 w/w%, depending slightly upon a place where it will be used, an existence of a processing step and the kind of resin.

The rodent-repellent resin composition in which the CHI microcapsules are mixed with the resin can be utilized in the forms of pellets, compounds and the like. Further, the rodent-repellent paste resin composition, in which the CHI microcapsules are dispersed in the resin and in which suitable additives such as a plasticizer and a dispersant are also added thereto, can be utilized in a direct manner, by coating therewith objects to be rendered rodent-repellent, by dipping them therein, or filling them therewith. Furthermore, with regard to the rodent-repellent resin composition prepared by first melting the resin at elevated temperature and then kneading the microcapsules into the molten resin, it can be utilized by molding it into a desired shape.

As be apparent from the foregoing, the rodent-repellent compositions containing the CHI microcapsules have the excellent rodent-repellent effect in themselves, and thus they can be employed as various rodent-repellent fillers and rodent repellent materials in a direct manner, in the state of a paste, or in a desirably molded shape.

One method for incorporating the CHI microcapsules into the resin comprises, for example, mixing the CHI microcapsules with the resin, melting the resultant mixture at elevated temperature, and kneading it.

The rodent-repellent resin composition thus obtained has the excellent rodent-repellent effect by itself, and can thus be used directly or in a desirably molded shape as a rodent-repellent filler, a rodent-repellent material and the like.

In the case that the rodent-repellent composition of the present invention is used as the rodent repellent material, the rodent-repellent resin composition itself may be molded, or already molded resin articles may be coated with the rodent-repellent resin composition by the use of a molding technique. In any case, an ordinary molding manner and a known molding apparatus in the art can be empolyed For example, the molding of the rodent-repellent resin composition can be accomplished by extrusion, injection molding, calendering or the like In this case, so long as the potency of the CHI microcapsules is not deteriorated, the conditions of the molding process can be suitably modified and changed for various use applications.

Examples of the thus molded rodent-repellent resin articles include linear articles such as electric wires and cables, hollow articles such as pipes, hoses, tubes and bags, and calendered articles such as tapes, sheets and tarpaulins for flexible containers.

In these rodent-repellent molded articles, a content of the CHI microcapsules is within the range of about 0.1 to 25 w/w% so as to obtain the rodent-repellent effect.

This constitution will be described in more detail. For example, when the rodent-repellent molded articles are the electric wires or cables, the CHI microcapsules are incorporated into insulating layers of the electric wires or sheaths of the electric cables so that the content of the CHI microcapsules may be within the range of about 0.1 to 25 w/w%, preferably about 0.17 to 20 w/w%, more preferably about 0.5 to 6.0 w/w%. Alternatively, the rodent-repellent electric wires or cables may be manufactured by forming the coating layers of the rodent-repellent resin composition on the insulating layers of the wires or on outer surfaces of the cables. Also in the case of the formation of the coating layers, the content of the CHI microcapsules should be in the same range as in the case of incorporating the microcapsules into the insulating layers or sheaths In each case, the electric wires or cables can be coated therewith in an ordinary manner which is employed in the field regarding the electric wire coating.

Rodent-repellent tapes, sheets and tarpaulins for flexible containers which are the rodent-repellent articles can be manufactured by directly calendering the rodent-repellent resin composition or by subjecting the composition to a laminate molding process. With regard to the rodent-repellent molded articles of the sheets, the CHI microcapsules are contained therein in an amount of about 0.1 to 25 w/w%, preferably about 0.17 to 20 w/w%, more preferably about 0.5 to 6.0 w/w%.

The rodent-repellent resin composition of the present invention can be suitably applied to various films (above all, films for agriculture), vinyl leathers, vinyl tiles and the like, in addition to the above-mentioned articles (Rodent-Repellent Coating Materials).

With regard to rodent repellent coating materials of the present invention, raw coating materials with which the CHI microcapsules will be mixed are not particularly limited.

Examples of the raw coating materials include, when classified by kinds of materials, oil coating materials, alcohol coating materials, cellulose coating materials, synthetic resin coating materials, aqueous coating materials, Japanese lacquer coating materials and rubber series coating materials. The above-mentioned oil coating materials include boiled oils, oil paints, oil varnishes and enamels; the alcohol coating materials include natural resin varnishes and synthetic resin varnishes; the cellulose coating materials include clear lacquers and lacquer enamels; the synthetic resin coating materials include aqueous coating material varnishes, synthetic resin enamels and polymer emulsion coating materials; the aqueous coating materials include aqueous paints, emulsion oil paints and polymer emulsion coating materials; the Japanese lacquer series coating materials include Japanese lacquer cashew varnishes; and the rubber series coating materials include rubber chloride coating materials, cyclized rubbers and synthetic rubber coating materials such as SBR and the like.

Above all, the synthetic resin varnishes are particularly preferable, and examples of them include phenolic resin varnishes, phthalic resin varnishes, maleic acid resin varnishes, urea resin varnishes, melamine resin varnishes, vinyl resin varnishes, epoxy resin varnishes, silicone resin varnishes, furan resin varnishes and polyester resin varnishes. Among these vanishes, the vinyl resin varnishes are particularly useful, and examples of them include vinyl acetate resin varnishes, vinyl chloride-vinyl acetate copolymer varnishes, styrene resin varnishes, acrylic resin varnishes and polyvinyl butyral varnishes.

The above-mentioned coating material, in practice, may contain a plasticizer, a drying agent, a curing agent, a dispersant, a skinning inhibitor, a thickener, a flatting agent, an anti-sagging agent, an antifungal agent, an ultraviolet absorbing agent and/or a pigment which is a secondary component for the formation of a coating film.

The rodent-repellent coating compositions in which the CHI microcapsules are mixed with or dispersed in the resin can be directly utilized as coating materials of electric wire cables for communication, signal and electric power, and in the form of vinyl chloride sheets for flexible containers. Further, the above-mentioned rodent-repellent coating materials may be applied on various bags made of papers, synthetic resins, cloths and the like as well as wall cloths, wall papers and architectual interior materials, thereby manufacturing rodent-repellent bags, rodent-repellent cloths and rodent-repellent interior materials.

The rodent-repellent articles coated with the rodent-repellent coating materials can be manufactured by the use of a usual coating technique, and examples of such coating techniques include brush coating, spray coating, electrostatic coating, electrodeposition and a printing technique such as screen printing In this case, a coating machine may be employed, and examples of usable coating machines include a blade coater, a gravure coater and air knife coater.

The rodent-repellent coating material is used in a CHI coating amount of about 0.05 to 2.0 g/m$^2$, preferably about 0.1 to 0.7 g/m$^2$, more preferably about 0.2 to 0.5 g/m$^2$. A content of CHI in the microcapsules and a content of the added or dispersed CHI microcapsules in the coating material should be decided taking an economical efficiency (coating amount) and a function of the formed coating film.

(Rodent-Repellent Adhesive)

In rodent-repellent adhesives of the present invention, raw adhesives with which the CHI microcapsules will be mixed are not particularly limited Examplary compositions of the usable adhesives include synthetic adhesives, rubber series adhesives and natural adhesives. The synthetic adhesives include resin series adhesives such as urea resins, melamine resins, phenolic resins, resorcinol resins, epoxy resins, polyurethanes, polyamides, vinyl acetate resins, vinyl chloride resins, polyvinyl alcohols and acrylic resins; the rubber series adhesives include chloroprene, nitrile rubbers, SBR, natural rubbers, reprocessed rubbers, butyl rubbers, polysulfide and silicone rubbers; and natural adhesives include glue and starch. Further, in addition thereto, the usable adhesives include polyisobutylenes, polyvinyl ethers, rubber chlorides, cellulose and asphalt series adhesives.

These adhesives which are particularly useful and manufactured in large quantities include urea resins, melamine resins, phenolic resin series, vinyl acetate resin series and synthetic rubber series adhesives.

The above-mentioned adhesive, in practice, may contain a solvent, a plasticizer, a resin, a thickener, a filler, a pigment, an antiseptic agent, an antioxidant, an antifoaming agent, and/or other desired additives.

The CHI microcapsules which are used in the present invention may be prepared in the undermentioned manner.

The rodent-repellent adhesives in which the CHI microcapsules are mixed with or dispersed into the raw adhesives can be directly utilized, in rodent-repellent bags and containers, for the sake of the adhesion of wall cloths, interior materials for architecture, paper bags, vinyl chloride sheets used for flexible containers. Further, the rodent-repellent adhesives may be employed, as rodent repellent adhesive tapes, by kneading the CHI microcapsules into the adhesives which normally have an adhesion and coating the vinyl chloride sheets with the rodent-repellent adhesives. Further, sealing mediums in which the CHI microcapsules are dispersed or contained can be utilized directly to repair cracks and to seal joints.

When the rodent-repellent adhesive of the present invention is used as a usual adhesive meterial, a main component of the adhesive may first be selected in compliance with an object to which adhesion will be made and the CHI microcapsules may be dispersed in or mixed with the selected main component in the process of preparing the adhesive, or alternatively the CHI microcapsules may be added to the adhesive at the time of its use.

Further, in the case that the rodent-repellent adhesive is used in the form of adhesive layers for tapes or tack papers, a predetermined amount of the CHI-filled microcapsules is first kneaded into the adhesive and is then applied on plastic sheets, papers or the like which are supports, by a coating technique in order to prepare the adhesive layers thereon, and the supports with the adhesive layers are cut into tapes or tack papers, which will be utilized by winding them onto the objects or causing them to adhere to the objects. By the use of such rodent-repellent adhesives, the rodent-repellent electric wires, rubber hoses for gases or vinyl chloride water pipes can easily be prepared by winding the rodent-repellent tapes or tack papers onto the wires, the hoses or the pipes in which the rodent repellent treatment has not been carried out. Furthermore, the damage of young fruit trees by rodents, when snowy, can also be prevented perfectly by winding the rodent-repellent tapes onto the young trees.

In the case that the rodent-repellent adhesive is utilized as a sealing medium, the CHI microcapsules are sufficiently kneaded into a liquid vehicle such as an oil, polybutene or an alkyd resin and a mineral filler such as calcium carbonate or asbestos as main components, thereby forming the rodent-repellent adhesive which can be used as the sealing medium.

The rodent-repellent adhesive is used in a CHI coating amount of about 0.05 to 3.0 g/m$^2$, preferably about 0.1 to 1.0 g/m$^2$, more preferably about 0.3 to 0.7 g/m$^2$.

A content of the CHI microcapsules in the adhesive should be decided considering a CHI concentration in the CHI microcapsules, a coating amount and its adhesive strength In order to further describe and illustrate the present invention, the following examples are provided It will be understood that these examples are provided for illustrative purposes and are not intended to be liminting of the scope of the invention as herein described and as set forth in the subjoined claims.

(Rodent-Repellent Microcapsules)

The following Examples 1 to 9 are connected with rodent-repellent microcapsules.

Example 1

In 120 g of dimethyl phthalate were dissolved 12 g of CHI (trade name Naramycin; Tanabe Seiyaku Co., Ltd.) and 13 g of terephthalic acid chloride in order to prepare a solution A. The solution A was emulsified in a 2% aqueous PVA (polyvinyl alcohol) solution to prepare an O/W emulsion On the other hand, 4 g of sodium carbonate and 8 g of diethylenetriamine were dissolved in 80 g of water to prepare a solution B. This solution B was slowly added to the above-mentioned O/W emulsion with stirring, and a reaction was continued with stirring for 24 hours, thereby producing microcapsules filled with 8% of CHI having polyamide walls.

Example 2

Dioctyl phthalate was substitued for dimethyl phthalate in Example 1, and microcapsules filled with CHI having polyamide walls were thereby prepared

Example 3

In 100 g of dioctyl phthalate were dissolved 25 g of diphenylmethane diisocyanate, 6 g of CHI, 12 g of polyoxypropylene ether and 100 g of methylene chloride in order to prepare a solution A. To 100 g of water were dissolved 20 g of gum arabic and 2.5 g of Turkey red oil to prepare a solution B. The above-mentioned solution A was emulsified in the solution B to prepare an O/W emulsion The thus obtained emulsion was reacted at 90° C. with stirring in order to form microcapsules filled with CHI having polyurethane walls.

Example 4

To 100 g of dimethyl phthalate were dissolved 2 g of CHI to prepare a solution A This solution A was emulsified in 400 g of a 2% aqueous gelatin solution to prepare an O/W emulsion. A pH of the thus obtained emulsion was adjusted to a level of 8 to 9 with a 10% aqueous sodium carbonate solution, and 50 g (in terms of solid content) of a ureaformaldehyde prepolymer (trade name Yuramin P; Mitsui Toatsu Chemicals, Inc ) were added thereto, and the pH was then adjusted to 5.0 with acetic acid A reaction was carried out at 50° C. for 2 hours with stirring in order to obtain microcapsules filled with CHI having urea resin walls.

Example 5

An epoxy resin (trade name Epicoat 815, molecular weight 330; Shell Petrochemical Co., Ltd.) was substituted for dimethyl phthalate in Example 4 in order to obtain CHI-filled microcapsules having urea resin walls.

Example 6

Dioctyl phthalate was substituted d for dimethyl phthalate in Example 4 in order to obtain CHI-filled microcapsules having urea resin walls.

Example 7

To 100 g of dimethyl phthalate were dissolved 5 g of CHI to prepare a solution A. This solution A was emulsified in 400 g of a 2% aqueous polyvinyl alcohol solution to prepare an O/W emulsion To the thus obtained emulsion were added 50 g (in terms of solid content) of a melamineformaldehyde prepolymer (trade name Sumirez Resin 607, syrup; Sumitomo Chemical, Co., Ltd.) with stirring, and its pH was then adjusted to 5.5 with a 20% aqueous citric acid solution. A reaction was carried out at 60° C. for 2 hours in order to obtain microcapsules filled with CHI having melamine resin walls.

Example 8

An epoxy resin (trade name Epicoat 828, molecular weight 380; Shell Petrochemical Co., Ltd.) was substituted for dimethyl phthalate in Example 7 in order to obtain CHI-filled microcapsules having melamine resin walls.

Example 9

Dimethyl phthalate was substituted for dimethyl phthalate in Example 7 in order to obtain CHI-filled microcapsules having melamine resin walls.

Table 1 given below sets forth potencies of CHI in the microcapsules one month after the encapsulation In this table, each potency means a percent of the remaining CHI in the microcapsules based on a charged CHI amount.

TABLE 1

| Example | Wall Material | Solvent for Core Material | Potency of CHI |
|---|---|---|---|
| 1 | Polyamide | Dimethyl phthalate | 52% |
| 2 | Polyamide | Dioctyl Phthalate | 53% |
| 3 | Polyurethane | Dioctyl Phthalate | 67% |
| 4 | Urea-Formaldehyde | Dimethyl Phthalate | 92% |
| 5 | Urea-Formaldehyde | Epoxy Resin | 90% |
| 6 | Urea-Formaldehyde | Dioctyl Phthalate | 93% |
| 7 | Melamine-Formaldehyde | Dimethyl Phthalate | 94% |
| 8 | Melamine-Formaldehyde | Epoxy resin | 89% |
| 9 | Melamine-Formaldehyde | Diethyl Phthalate | 91% |

MEASUREMENT OF POTENCIES OF CHI IN CAPSULES

In an agate mortar, about 0.5 g of prepared microcapsules (powder) filled with CHI was ground down, and CHI was extracted therefrom with acetone. Afterward, an amount of CHI was measured in accordance with official methods of analysis of the agricultural chemicals "Preparations containing cycloheximide as the main component".

The aforesaid results of Examples 4 to 9 indicate that the microcapsules filled with CHI of the present invention are extremely excellent in the stability of CHI and the retention of the CHI potencies with time.

Example 10

Each conductor having 7 strands and a core outer diameter of 3.5 mm was coated with an insulating layer comprising a polyvinyl chloride composition so that a thickness of the insulating layer might be 1.0 mm, whereby a control cable was made. Three of the control cables were intertwined into one another, and the thus intertwined cable was coated with a protective layer having a thickness of 1.0 mm and a rodent-repellent vinyl chloride composition layer thereon comprising the following formulation and having a thickness of 0.5 mm by means of a co-extrusion technique (simultaneous multi-layer extrusion coating; conditions: 160° C. and 5 minutes) in order to obtain the rodent-repellent vinyl chloride coating cable.

| Component | Parts by Weight |
|---|---|
| Vinyl Chloride (Average Polymerization Degree 1300) | 100 |
| Dioctyl Phthalate | 50 |
| Polymerized Organic Tin Mercapto Compound | 5 |
| Lead Stearate | 1 |
| 8% CHI Microcapsules (CHI content in the composition 0.25%) | 5 |

TEST FOR STABILITY OF CHI ON COATING PVC CABLE WITH RODENT-REPELLENT COMPOSITION (Procedure 1)

For the purpose of inspecting the stability of the CHI, the same procedure as in Example 10 was repeated, but in Control 1, the CHI microcapsules were not used; in Control 2, 0.7% of a CHI crystal was substituted for the CHI microcapsules; in COntrol 3, 0.5% of the CHI crystal was substituted for the CHI microcapsules. The results are set forth in Table 2.

TABLE 2

|  | Present Invention | Control 1 | Control 2 | Control 3 |
|---|---|---|---|---|
| Theoretical Content of Charged CHI | 0.25% | 0 | 0.7% | 0.5% |
| Measured Content of CHI | 0.19% | 0 | 0.21% | 0.12% |
| Residue Percent of CHI | 75% | 0 | 30.0% | 24.0% |

MEASUREMENT OF CHI

A part of the rodent-repellent coating layer of each cable in which CHI was blended was peeled off therefrom, and 10 ml of acetone were then added to 1 g of the peeled coating layer. After the resultant mixture had been allowed to stand for 24 hours, 10 ml of methanol were added thereto and heated up to 70° C. It was afterward allowed to stand for 1 hour and measured in accordance with the official methods of analysis of the agricultural chemicals "Preparations containing cycloheximide as the main component" (the same may be applied to the following).

TEST FOR PRESERVATIVE STABILITY OF CHI IN PVC RODENT-REPELLENT CABLE (Procedure 2)

A part of the rodent-repellent coating layer about the cable prepared by the above-mentioned Procedure 1 was cut out therefrom, and a preservative stability of the coating layer was inspected under the conditions of a temperature of 50° C. and a relative humidity of 85%. The results are set forth in Table 3.

TABLE 3

|  | Present Invention | Control 1 | Control 2 | Control 3 |
|---|---|---|---|---|
| Initial Content of CHI | 0.19% | 0 | 0.21% | 0.12% |
| Residue Percent of CHI |  |  |  |  |
| Initial | 100% | 0 | 100% | 100% |
| 1 Month | 100% | 0 | 83% | 78% |
| 2 Months | 98% | 0 | 71% | 57% |
| 3 Months | 99% | 0 | 65% | 47% |

RAT-REPELLING EFFECT OF PVC RODENT-REPELLENT CABLES (Procedure 3)

The respective cables obtained in the above-mentioned Procedure 1 were cut off to prepare samples each having a length of 20 cm, and these samples were placed in a breeding cage in which there were two male and three female Wister Rats. Feeds and drinking water were given thereto and the samples were allowed to stand for 24 hours and for 48 hours AFterward, the respective cables were taken out therefrom and a nibble damage state of the samples by the rats was observed. The results are set forth in Table 4.

TABLE 4

|  | Present Invention | Control 1 | Control 2 | Control 3 |
|---|---|---|---|---|
| Initial Content of CHI | 0.19% | 0 | 0.21% | 0.12% |
| Exposure Percent of Core Wire |  |  |  |  |
| 24 Hours Tooth Traces | 97% | 16% | 82% |  |
| 48 Hours Tooth Traces | 100% | 100% | 100% |  |

Note: Each value above mentioned is represented by a length percent of the exposed wire based on the length of each specimen, i.e., 20 cm.

TEST FOR TRANSFER OF CHI TOWARD INNER SHEATH (PROTECTIVE) LAYERS OF PVC CABLES (Procedure 4)

The cables obtained in the above-mentioned Procedure 1 were allowed to stand at room temperature (23° C.), and amounts of CHI which had been transferred to the inner protective layers were measured. The results are set forth in Table 5.

TABLE 5

|  | Present Invention | Control 2 | Control 3 |
|---|---|---|---|
| Initial Content of CHI | 0.19% | 0.21% | 0.12% |
| CHI Conc. in Sheaths |  |  |  |
| Initial | Trace | Trace | Trace |

TABLE 5-continued

|  | Present Invention | Control 2 | Control 3 |
|---|---|---|---|
| 3 months | Trace | 0.012% | 0.005% |
| 6 months | Trace | 0.017% | 0.006% |

TEST FOR BLEEDING OF CHI FROM PVC CABLES (Procedure 5)

The respective cables obtained by the above-mentioned Procedure 1 were allowed to stand under conditions of a temperature of 50° C. and a relative humidity of 85%, and amounts of CHI which had bled onto the surfaces of the cables were measured. The results are set forth in Table 6.

TABLE 6

|  | Present Invention | Control 2 | Control 3 |
|---|---|---|---|
| Initial Amount of CHI | 0.19% | 0.21% | 0.12% |
| Amounts of CHI Bled onto Surfaces (Percent of CHI Based on Initial Contents thereof) | | | |
| 1st day | Trace | 3.4% | 3.1% |
| 2nd day | Trace | 3.7% | 3.6% |
| 3rd day | Trace | 3.4% | 3.6% |
| 4th day | Trace | 4.2% | 3.3% |
| 5th day | Trace | 4.0% | 3.0% |

MEASUREMENT OF CHI

On the surface of a culture medium containing test organisms, Saccharomyces cerevisiae, each specimen was rolled for 5 minutes to contact it with the medium. Afterward, an incubation was carried out at 32° C. for 16 hours. An amount of CHI in each specimen was measured on the basis of an area of inhibition zones formed on the surface of the culture medium. cTEST FOR WATER RESISTANCE OF CHI IN PVC CABLES (Procedure 6)

The respective cables obtained in the above-mentioned Procedure 1 were cut off to prepare specimens each having a length of 3 cm, and each specimen was placed in a 200 ml beaker and 100 ml of water were then added thereto. The beakers were but in a water bath temperatures of which were adjusted to 30 and 50° C., and after a certain period of time has elapsed, the cables were taken out and amounts of the remaining CHI therein were measured. The results are set forth in Table 7.

TABLE 7

|  | Present Invention | | Control 2 | | Control 3 | |
|---|---|---|---|---|---|---|
| Initial Content of CHI | 0.19% | | 0.21% | | 0.12% | |
| Residue Percent of CHI in Cable Based on Initial Content thereof | | | | | | |
|  | 30° C. | 50° C. | 30° C. | 50° C. | 30° C. | 50° C. |
| 1st Day | 96.6% | 94.0% | 97.0% | 84.0% | 92.0% | 72.0% |
| 3rd Day | 98.3% | 92.0% | 93.0% | 57.0% | 89.0% | 58.0% |
| 6th Day | 97.0% | 89.0% | 88.0% | 12.0% | 71.0% | 14.0% |

Example 11

A coating material was prepared in accordance with the following formulation. The thus prepared coating material would be utilized to manufacture PVC tarpaulins for flexible containers.

| | Formulation (w/w %) | | |
|---|---|---|---|
|  | Example 1 | Control 2 | Control 3 |
| Vinyl Chloride/Acrylic Acid Copolymer Resin* | 20 | 20 | 20 |
| Toluene | 35 | 35 | 35 |
| Methyl Ethyl Ketone | 31.5 | 43 | 42 |
| 15% CHI Microcapsules | 13.5 | — | — |
| CHI Crystal | — | 2 | 3 |
|  | 100 | 100 | 100 |
| CHI Content (%) | 2.0 | 2.0 | 3.0 |

* VC:AC = 15:85, P; 420

A polyvinyl chloride composition having a formulation mentioned below was applied on a polyester base cloth which was a core material, by means of a calender processing technique in order to prepare tarpaulins for flexible containers. Afterward, the tarpaulins were coated, on either side of each, with the rodent-repellent coating material which had been prepared in Example 11, with stirring by the use of a gravure coating technique so that a coating amount of the rodent-repellent coating material might be as much as 13 g per square meter of the tarpaulin sheets. The thus treated tarpaulin sheets were then dried at a temperature of 80° C. for 2 minutes, thereby obtaining the rodent-repellent tarpaulins for the flexible containers.

| Formulation of Polyvinyl Chloride Composition | |
|---|---|
| Polyvinyl Chloride (Average Polymerization Degree 1,450) | 100 Parts by Weight |
| Dioctyl Phthalate | 25 Parts by Weight |
| Dibutyl Phthalate | 20 Parts by Weight |
| Chlorinated Paraffin | 10 Parts by Weight |
| Basic Lead Carbonate | 5 Parts by Weight |
| Lead Stearate | 1 Parts by Weight |

TEST FOR PRESERVATIVE STABILITY OF CHI ON RODENT-REPELLENT TARPAULINS FOR FLEXIBLE CONTAINERS (Procedure 7)

For the purpose of inspecting the preservative stability of the CHI on the PVC parpaulins under conditions of a temperature of 50° C. and a relative humidity of 85%, the same procedure as in Example 11 was repeated to carry out a rodent-repellent application processing, but in Control11, the CHI microcapsules were not used; :n Control 2, 2% of a CHI crystal was substituted for the CHI microcapsules; in Control 3, 3% of the CHI crystal was substituted for the CHI microcapsules. The results are shown in Table 8. In this table, the unit of theoretical and measured values of CHI is $\mu g/cm^2$.

TABLE 8

| | Elapsed Days | Present Invention | Control 1 | Control 2 | Control 3 |
|---|---|---|---|---|---|
| Theoretical Value of CHI | — | 26.3 | 0 | 26.0 | 39.0 |
| Measured |  | 25.3 | 0 | 26.5 | 35.1 |

TABLE 8-continued

|  | Elapsed Days | Present Invention | Control 1 | Control 2 | Control 3 |
|---|---|---|---|---|---|
| Value of CHI |  |  |  |  |  |
| Residue Percent of CHI (%) |  |  |  |  |  |
|  | Initial | 100 | 0 | 100 | 100 |
|  | 1 Week | 99 | 0 | 96 | 91 |
|  | 2 Weeks | 101 | 0 | 95 | 87 |
|  | 3 Weeks | 97 | 0 | 85 | 81 |

TENTATIVE MEASUREMENT OF CHI

To 1 g of the rodent-repellent processed tarpaulin were added 10 ml of acetone, and the resultant mixture was allowed to stand at room temperature for 24 hours Afterward, 10 ml of methanol were added thereto and heated up to 70° C., and it was then allowed to stand for 1 hour in order to prepare a sample. The thus prepared sample was measured in accordance with the official methods of analysis of the agricultural chemicals (Preparations containing CHI as the main component) (the same may be applied to the following).

RAT-REPELLING EFFECT OF RODENT-REPELLENT TARPAULINS FOR PVC FLEXIBLE CONTAINERS (Procedure 8)

Each of the tarpaulins obtained in the above-mentioned Procedure 7 was cut to form a 75mm×150mm fragment, and two solid feed lumps for rats were wrapped in the fragment and the thus prepared parcel was stapled at its outer peripheral positions by staples to prepare a sample. This sample was placed in a breeding cage in which there were three Wister Rats which had fasted for 24 hours and which had a body weight of about 500 g. After it had been allowed to stand therein overnight, it was taken out and its nibbling state was observed. The five cages were employed The results are set forth in Table 9. In this table, the unit of an initial potency is $\mu g/cm^2$.

TABLE 9

|  | Present Invention | Control 1 | Control 2 | Control 3 |
|---|---|---|---|---|
| Initial Potency of CHI | 25.3 | 0 | 26.5 | 35.1 |
| Nibbling State | — | ++++ | +++ | — |
| Feed Loss (%) | 0 | 100 | 70 | 0 |

—: Only tooth traces, no nibble damage.
+: Partially pierced.
++: Area of pierced portions of the sheet being 1/10 or less.
+++: It being 2/10 or less.
++++: It being more than 2/10.

TEST FOR TRANSFER OF CHI TOWARD TARPAULINS FOR PVC FLEXIBLE CONTAINERS (Procedure 9)

The tarpaulins obtained in the above-mentioned Procedure 7 were allowed to stand at room temperature, and amounts of CHI which had been transferred to the tarpaulin bodies were measured. The results are set forth in Table 10. In this drawing, the unit of a potency is $\mu g/cm^2$.

TABLE 10

|  | Present Invention | Control 2 | Control 3 |
|---|---|---|---|
| Initial Potency of CHI | 25.3 | 26.5 | 35.1 |
| Amounts of Bled CHI on Back Surfaces of Sheets Elapsed Days |  |  |  |
| Initial | 0 | 0 | 0 |
| 3 Months | 0 | + | ++ |
| 6 Months | 0 | ++ | ++ |

+: 0.5 $\mu g/cm^2$ in terms of CHI
++: 1.0 $\mu g/cm^2$ in terms of CHI

TENTATIVE MEASUREMENT OF CHI

On the surface of a culture medium containing test organisms, Saccharomyces cerevisiae, each specimen was rolled for 5 minutes to contact it with the medium. Afterward, a cultivation was carried out at 32° C. for 16 hours. The amount of CHI in each specimen was measured from an area of inhibition zones formed on the surface of the culture medium.

TEST FOR WATER RESISTANCE OF CHI IN RODENT-REPELLENT TARPAULINS FOR PVC FLEXIBLE CONTAINERS (Procedure 10)

The respective tarpaulins obtained in the above-mentioned Procedure 7 were cut off to make a 100×100 mm² sheet and then to prepare four specimens each having a length of 5 cm, and each specimen was placed in a 200-ml beaker and 100 ml of water were then added thereto. The beakers were put in two water baths temperatures of which were adjusted to 30 and 50° C., and after certain periods of time had elapsed, 5 ml solutions in the beakers were taken out therefrom and amounts of the dissolved CHI therein were measured. Amounts of CHI on the tarpaulins were measured in accordance with the above-mentioned Procedure 7. The results are set forth in Table 11 In this drawing the unit of a potency is $\mu g/cm^2$.

TABLE 11

|  | Present Invention | | Control 2 | | Control 3 | |
|---|---|---|---|---|---|---|
| Initial Potency of CHI | 25.3 | | 26.5 | | 35.1 | |
| Percent of CHI dissolved out in Water Base on Initial Potency thereof | | | | | | |
|  | 30° C. | 50° C. | 30° C. | 50° C. | 30° C. | 50° C. |
| 30 Min | 2 | 2 | 8 | 17 | 11 | 15 |
| 60 Min | 2 | 2 | 11 | 25 | 17 | 27 |
| 120 Min | 3 | 4 | 23 | 37 | 25 | 33 |
| 180 Min | 3 | 5 | 28 | 54 | 32 | 49 |
| 240 Min | 4 | 7 | 33 | 63 | 41 | 65 |
| Residue Percent of CHI in Tarpaulin | 96 | 93 | 67 | 37 | 59 | 35 |

Example 12

CHI microcapsules were dispersed into and mixed with an acrylic resin adhesive for adhesive processing in accordance with the following formulation:

| Components | Parts by Weight |
|---|---|
| Acrylic Resin Adhesive for Adhesive Processing (trade name S-dine 395c; Sekisui Chemical Co., Ltd.; solid content 40%) | 100 |
| 15% CHI microcapsules | 20 |

TEST FOR CHI STABILITY OF RODENT-REPELLENT ADHESIVE LAYER (Procedure 11)

A sample for Comparative Example 1 was prepared by using 2.56 parts by weight of a CHI crystal in place of the CHI microcapsules in Example 12.

Adhesive layers were formed from the rodent-repellent adhesives of Example 12 and Comparative Example 1, and were allowed to stand under conditions of a temperature of 50° C. and a relative humidity of 85% for 3 weeks. To about 1 g of each sample were added 10 ml of acetone and the resultant mixture was allowed to stand for 24 hours, and 10 ml of methanol were then added thereto. Afterward, the mixture was heated up to 70° C. and was allowed to stand for 1 hour. Its filtrate was a sample. A CHI amount in each sample was measured in accordance with the official methods of analysis of the agricultural chemicals (Preparations containing CHI as a main component). The results are set forth in Table 12.

TABLE 12

|  | Theoretical Content of Charged CHI | Measured Content of CHI | Residual Percent of CHI |
|---|---|---|---|
| Example 12 | 5.0% | 5.0% | 100.0% |
| Comparative Example 1 | 6.0% | 5.07% | 84.5% |

TEST FOR RAT-REPELLING EFFECT OF RODENT-REPELLENT ADHESIVE PROCESSED ARTICLES (Procedure 12)

Flexible vinyl chloride sheets each having a thickness of 0.1 mm were coated with the rodent-repellent adhesives in Example 12 and Comparative Example 1, and with the acrylic resin adhesive (Control 1) used in Example 12 and Comparative Example 1 by means of a wire bar so that their coating amounts may be 20 g per square meter These coated sheets were air-dried for 10 minutes or more in order to prepare rodent-repellent tapes and other tapes which were not rodent-repellent. These tapes were wound onto PVC cables and were allowed to stand under conditions of a temperature of 50° C. and a relative humidity of 85% for 3 weeks to prepare samples These samples were placed in a breeding cage in which there were one wild bear rat which had fasted for 24 hours and which had a body weight of about 500 g, and they were allowed to stand overnight. Afterward, the PVC cables were taken out therefrom, and a nibble damage state thereof was observed The results are set forth in Table 13.

TABLE 13

|  | Example 12 | Comparative Example 1 | Control 1 |
|---|---|---|---|
| Theoretical Amount of Charge CHI ($\mu g/cm^2$) | 50 | 50 | 0 |
| Measured Amount of CHI ($\mu g/cm^2$) | 50 | 39 | 0 |
| Nibbling State | − | +++ | ++++ |
| Exposure Percent of Core Wire of PVC Cable | 0 | 15 | 95 |

−: Only tooth trace, no nibble damage.
+: Partially pierced.
++: Area of nibbled portions of cables being 1/10 or less.
+++: It being 2/10 or less.
++++: It being more than 2/10.

TEST FOR PRESERVATIVE STABILITIES OF CHI IN ADHESIVE LAYERS (Procedure 13)

For the adhesive tape which were the articles made by the use of the rodent-repellent adhesives prepared in Example 12 and Comparative Example 1, a preservative stability was inspected.

The adhesive tapes were exposed under conditions of a temperature 50° C. and a relative humidity of 85%, and amounts of CHI therein were measured to seek the preservative stabilities of the adhesive layers. The results are set forth in Table 14.

TABLE 14

|  | Example 12 | Comparative Example 1 |
|---|---|---|
| Theoretical Amount of Charge CHI ($\mu g/cm^2$) | 50 | 50 |
| Measured Amount of CHI ($\mu g/cm^2$) | 50 | 39 |
| Residue Percent of CHI |  |  |
| Initial | 100 | 100 |
| 2 Months | 99.0 | 50.1 |
| 3 Months | 96.3 | 29.3 |

CONCLUSION

The rodent-repellent preparations, and the rodent-repellent resin compositions, coating materials and adhesives of the present invention comprise microcapsules which are filled with the solution containing CHI as the core material, and they have the excellent rodent-repelling effect by themselves. Therefore, they can be widely utilized as rodent-repellent materials directly or by kneading them into various objects, coating, blowing, dipping, laminating, filling, winding or the like.

Further, since the core material of the microcapsules is the CHI solution, the latter will diffuse extremely rapidly in rodents' saliva, when they nibble the microcapsules. Accordingly, the taste of the core material can function effectively, and the repelling effect of the products according to the present invention can be more heightened than conventional CHI crystals, with the result that, for example, its dose itself can be more largely reduced than the conventional CHI crystals Also in the case that the rodent-repellent resin compositions of the present invention are utilized by forming them into various shapes, the CHI in the rodent-repellent resin compositions is protected by the wall material of the capsules, and thus the potency of CHI will not be lowered by heat at molding or by a by-product such as hydrogen chloride. In consequence, in the preparations according to the present invention, an excessive amount of CHI need not be charged to compensate for a presumptive amount of CHI which will be decomposed under used conditions, which fact permits not only that they are several times more economical but also that they are used even in resin fields to which the conventional CHI crystals cannot be applied. For example, the rodent-repellent preparations of the present invention are not dissolved out by the function of a plasticizer which is often blended in vinyl resins, and thus there does not occur any bleeding phenomenon of CHI onto the surfaces of objects and to the resin protective layers of objects to be coated. It is fair to say that the preparations of the present invention can retain the excellent rodent-repelling effect for a long periof of time.

In addition thereto, in the rodent-repellent coating materials and adhesives of the present invention, the microcapsules filled with CHI are used, and thus the potency of CHI will not be deteriorated by water or other solvents in coating materials and adhesives dispersed thereinto, mixed therewith or kneaded thereinto. Moreover, CHI can be safely protected from curing agents to be added to the coating materials and adhesives, and heat to be applied to them, and even after the objects have been coated with CHI, the latter will not be dissolved out by rain water and the like. This fact permits the rodent-repellent preparations of the present invention to remain effective for a long period of time.

Additionally, since making use of the microcapsules filled with CHI, the preparations of the present invention are improved in safety and are also convenient from the sanitary viewpoint at the times of manufacturing and handling as well as in point of a food hygiene at using.

What is claimed is:

1. Rodent-repellent microcapsules in which a core material is coated with a wall material of said microcapsules, said core material being a solution of cycloheximide in a high-boiling solvent selected from the group consisting of phthalates, adipates, sebacates, phosphates, and epoxy resins having an average molecular weight of 400 or less, and said cycloheximide being represented by the formula:

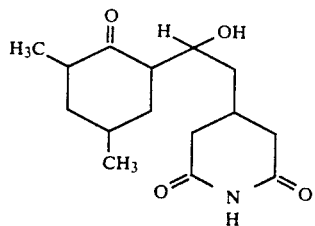

2. The microcapsules of claim 1 wherein said high-boiling solvent contains cycloheximide in an amount of about 0.25 to 50 w/w% based on said microcapsules.

3. The microcapsules of claim 2 wherein said high-boiling solvent is a phthalate selected from the group consisting of dimethyl phthalate, diethyl phthalate, dibutyl phthalate, diheptyl phthalate, dioctyl phthalate, diisodecyl phthalate, butyl benzyl phthalate, dimethyl isophthalate, di-2-ethylhexyl phthalate, and ditridecyl phthalate.

4. The microcapsules of claim 2 wherein said high-boiling solvent is an adipate selected from the group consisting of diisobutyl adipate and dioctyl adipate.

5. The microcapsules of claim 2 wherein said high-boiling solvent is a sebacate selected from the group consisting of dibenzyl sebacate and dioctyl sebacate.

6. Rodent-repellent microcapsules comprising:
a microcapsule wall; and
a core solution of 2-20% by weight of cycloheximide in a high-boiling solvent selected from the group consisting of phthalates, adipates, sebacates, phosphates, and epoxy resins having an average molecular weight of no more than 400.

7. The microcapsules of claim 6 wherein said high-boiling solvent is a phthalate selected from the group consisting of dimethyl phthalate, diethyl phthalate, dibutyl phthalate, diheptyl phthalate, dioctyl phthalate, diisodecyl phthalate, butyl benzyl phthalate, dimethyl isophthalate, di-2-ethylhexyl phthalate, and ditridecyl phthalate.

8. The microcapsules of claim 6 wherein said high-boiling solvent is an adipate selected from the group consisting of diisobutyl adipate and dioctyl adipate.

9. The microcapsules of claim 6 wherein said high-boiling solvent is a sebacate selected from the group consisting of dibenzyl sebacate and dioctyl sebacate.

10. A rodent-repellent resin composition comprising a resin and rodent-repellent microcapsules in which a core material is coated with a wall material of said microcapsules, said core material being a solution of cycloheximide in a high-boiling solvent selected from the group consisting of phthalates, adipates, sebacates, phosphates, and epoxy resins having an average molecular weight 400 or less, and said cycloheximide being represented by the formula:

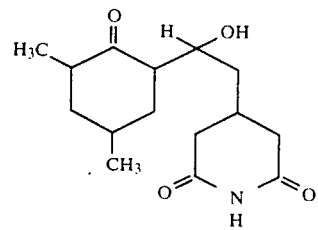

11. The composition of claim 10 wherein said high-boiling solvent contains cycloheximide in an amount of about 0.25 to 50 w/w% based on said microcapsules.

12. The composition of claim 11 wherein said high-boiling solvent is a phthalate selected from the group consisting of dimethyl phthalate, diethyl phthalate, dibutyl phthalate, diheptyl phthalate, dioctyl phthalate, diisodecyl phthalate, butyl benzyl phthalate, dimethyl isophthalate, di-2-ethylhexyl phthalate, and ditridecyl phthalate.

13. The composition of claim 11 wherein said high-boiling solvent is an adipate selected from the group consisting of diisobutyl adipate and dioctyl adipate.

14. The composition of claim 11 wherein said high-boiling solvent is a sebacate selected from the group consisting of dibenzyl sebacate and dioctyl sebacate.

15. A rodent-repellent coating material comprising a rodent-repellent microcapsules in which a core material is coated with a wall material of said microcapsules, said core material being a solution of cycloheximide in a high-boiling solvent selected from the group consisting of phthalates, adipates, sebacates, phosphates, and epoxy resins having an average molecular weight of 400 or less, and said cycloheximide being represented by the formula:

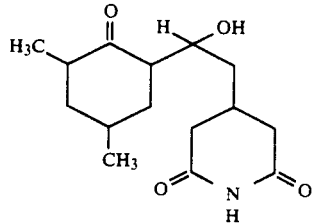

16. The rodent-repellent coating material of claim 15 wherein said high-boiling solvent contains cyclohexi-mide in an amount of about 0.25 to 50 w/w% based on said microcapsules.

17. The rodent-repellent coating material of claim 16 wherein said high-boiling solvent is a phthalate selected from the group consisting of dimethyl phthalate, diethyl phthalate, dibutyl phthalate, diheptyl phthalate, dioctyl phthalate, diisodecyl phthalate, butyl benzyl phthalate, dimethyl isophthalate, di-2-ethylhexyl phthalate, and ditridecyl phthalate.

18. The rodent-repellent coating material of claim 16 wherein said high-boiling solvent is an adipate selected from the group consisting of diisobutyl adipate and dioctyl adipate.

19. The rodent-repellent coating material of claim 16 wherein said high-boiling solvent is a sebacate selected from the group consisting of dibenzyl sebacate and dioctyl sebacate.

* * * * *

UNITED STATES PATENT AND TRADEMARK OFFICE
CERTIFICATE OF CORRECTION

PATENT NO. : 5,002,768
DATED : March 26, 1991
INVENTOR(S) : Takeshi Kondo, et al.

It is certified that error appears in the above-identified patent and that said Letters Patent is hereby corrected as shown below:

Column 10, line 3, "substituted d" should read --substituted--.

Column 11, line 39, "COntrol" should read --Control--.

Column 12, line 35, "hours AFterward," should read --hours. Afterward--.

Column 13, line 40, "cTEST" should read --TEST--.

Column 13, line 50, "but" should read --put--.

Column 14, line 54, "Control11," should read --Control 1,--.

Column 14, line 55, ":n" should read --in--.

Column 18, line 6, "Charge" should read --Charged--.

Column 18, line 22, "tape" should read --tapes--.

Column 18, line 37, "Charge" should read --Charged--.

UNITED STATES PATENT AND TRADEMARK OFFICE
CERTIFICATE OF CORRECTION

PATENT NO. : 5,002,768

DATED : March 26, 1991

INVENTOR(S) : Takeshi Kondo, et al.

It is certified that error appears in the above-identified patent and that said Letters Patent is hereby corrected as shown below:

Column 19, line 1, ";n" should read --in--.

Column 20, line 65, Claim 15, "A rodent-repellent coating material comprising a rodent" should read --A rodent-repellent coating material comprising a <u>resin, one or more solvents and</u> rodent-repellent--.

Signed and Sealed this

Twelfth Day of October, 1993

Attest:

BRUCE LEHMAN

Attesting Officer     Commissioner of Patents and Trademarks